United States Patent [19]

Chiarizzio et al.

[11] Patent Number: 4,601,289
[45] Date of Patent: Jul. 22, 1986

[54] FEMORAL TRIAL PROSTHESIS/RASP ASSEMBLY

[75] Inventors: Samuel J. Chiarizzio; Kenneth W. Russell, both of Memphis, Tenn.

[73] Assignee: Dow Corning Wright, Arlington, Tenn.

[21] Appl. No.: 719,785

[22] Filed: Apr. 2, 1985

[51] Int. Cl.⁴ .................... A61F 17/32; A61F 5/04; A61F 2/36
[52] U.S. Cl. ................... 128/305; 128/92 E; 128/92 EC; 623/23
[58] Field of Search ........... 128/92 E, 92 EB, 92 EC, 128/92 H, 305; 623/16, 18, 22, 23

[56] References Cited

U.S. PATENT DOCUMENTS

| | | | |
|---|---|---|---|
| 3,818,514 | 6/1974 | Clark | 623/23 |
| 3,857,389 | 12/1974 | Amstutz | 128/92 EC |
| 4,306,550 | 12/1981 | Forte | 128/92 E |
| 4,552,136 | 11/1985 | Kenna | 128/92 E |

FOREIGN PATENT DOCUMENTS 0122670 10/1984 European Pat. Off. .......... 128/92 E

OTHER PUBLICATIONS

Brochure—"The Total System", Zimmer, USA Inc., Warsaw IN, pp. 19-23.
Brochure—"Trunnion-Head Total Hip, Operative Technique", No. 5104, Allo Pro AG, Dorfstrasse 13, CH-6340. Baar/Zug, Item 16 described on 2 pages and picture of Art. Nr. 5104, 5105, 5106.
Brochure—"The PCA(TM) Total Hip System", No. H4139 15M 1/84 B, pp. 8, 14-17 and 43, and pp. 42-49 of the Surgical Procedure in that Brochure, Howmedica, Inc., Rutherford, N.J.
Brochure—"CFE Taperloc Hip System Surgical Technique", No. Y-BMT-010/090183, 3 pages, Biomet, Inc., Warsaw, IN.
Brochure—"The AML(TM) Total Hip System with Porocoat(R)", No. 20M1183 0611-52, DePuy, Inc., Warsaw, IN, 3 pages (1983).
Brochure—"The Poro Metal Cementless Total Hip Prosthesis", pp. 43, 44, 90 and 91, distrib.: Daumer, Intl., West Germany.
Brochure—"The Bio-Fit(TM) Stem", No. 6893, Richards Medical Co., Memphis, TN, 6 pages (1985).
Brochure—"Series II Total Hip System", No. 3037, Richards Mfg. Co., Inc., Memphis, TN, pp. 15, 16, 25 (1978).
Catalog p. A-11, Punch No. 2170-00, DePuy, Inc., Warsaw, IN, (1980).

Primary Examiner—Ronald L. Frinks
Attorney, Agent, or Firm—Richard E. Rakoczy

[57] ABSTRACT

This invention relates to a femoral trial prosthesis/rasp assembly for use in hip implant surgery. The novel handle assembly grips the combination trial prosthesis/rasp in a secure manner by clamping over and locking onto a post on the trial prosthesis/rasp which later serves as a mounting piece for a femoral prosthesis head used in trial reductions. The handle assembly preferably comprises a straight member which has a recess for reception of one half of the post and a pivotable lever which contains an opposing recess which fits over the remainder of the post when a screw is tightened to bring the two recesses together over the post. The trial prosthesis/rasp is cooperatively engaged by a projection located at the end of the handle assembly to hold the trial prosthesis/rasp in a preselected orientation with respect to the handle assembly during use. The trial prosthesis/rasp is easily released from the handle by turning the screw to permit the lower portion of the straight member and lever to separate.

6 Claims, 7 Drawing Figures

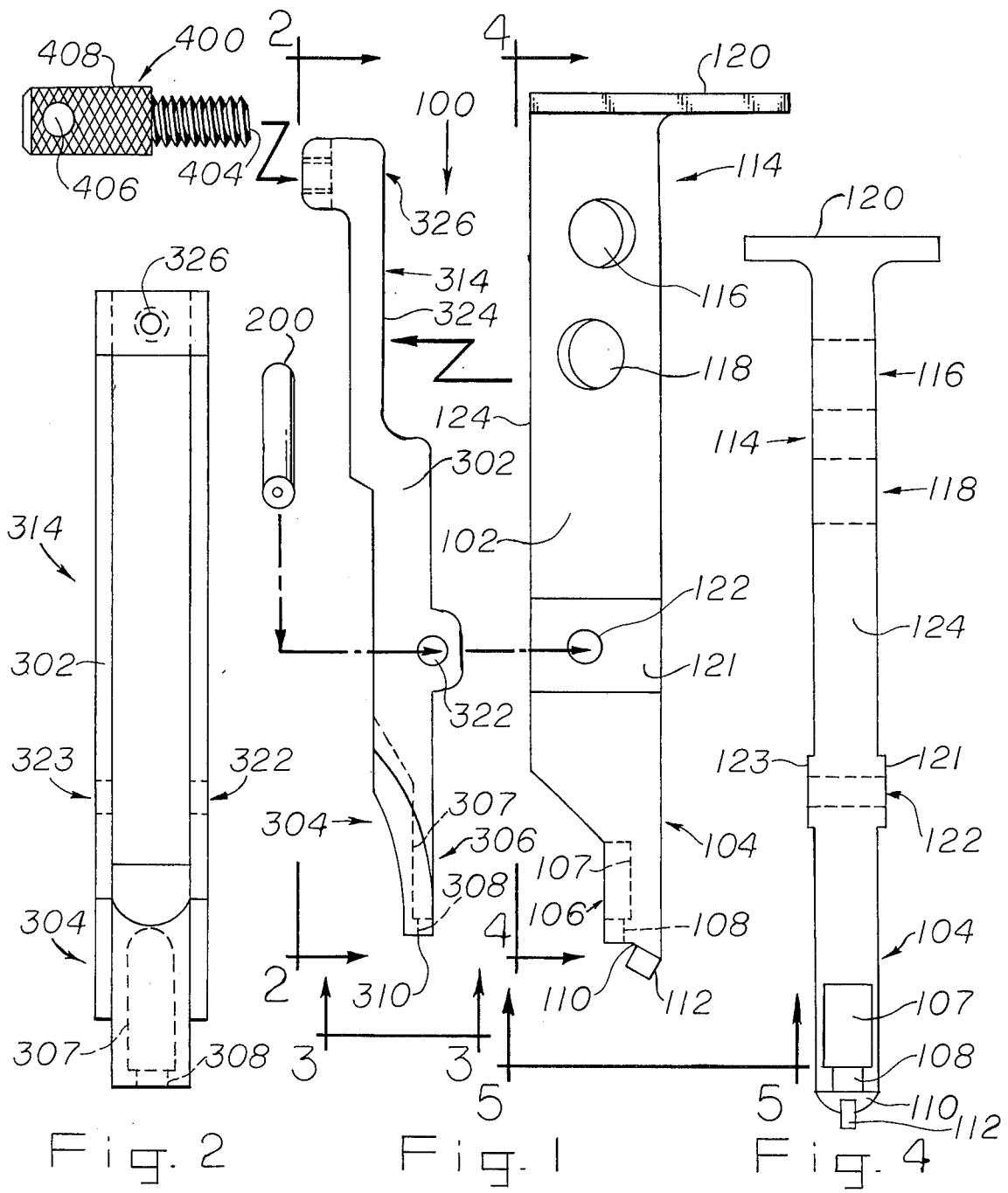

FEMORAL TRIAL PROSTHESIS/RASP ASSEMBLY

BACKGROUND OF THE INVENTION

This invention relates to an instrument for preparing the proximal femur to receive a proximal femoral prosthesis. The instrument is a combination of a novel handle assembly for securely holding a trial prosthesis/rasp which is used to prepare the femur. The handle assembly is then removed leaving the trial prosthesis/rasp in the femur to accomplish trial reduction of the hip joint.

During hip surgery involving the replacement of the proximal femoral head using a proximal femoral prosthesis, the proximal femur must be prepared to receive the stem of the proximal femoral prosthesis. A number of techniques have been developed to accomplish the insertion of such prosthesis, and such techniques typically involve the use of a rasp to accomplish the shaping of the proximal femur. Some techniques employ a rasp attached to a handle which is only used to prepare a socket in the proximal femur. A separate trial prosthesis is then inserted in the socket to accomplish reduction (i.e., proper sizing of a permanent femoral implant).

To achieve the best fixation of the permanent femoral implant, it has become a common practice to employ a combination femoral trial prosthesis/rasp to prepare the socket. The trial prosthesis/rasp is then left in the socket and a femoral prosthesis head is placed on a post extending from the trial prosthesis/rasp to accomplish reduction. The post may also be used to assist in preparation of the calcar surface. The trial prosthesis/rasp is then removed and a permanent femoral prosthesis is inserted into the prepared socket which remains basically unchanged since the rasping procedure was completed.

A number of instruments to hold the trial prosthesis/rasp have been suggested. It is important that the trial prosthesis/rasp be held rigidly. U.S. Pat. No. 4,306,550 to Forte (issued Dec. 22, 1981) shows a handle containing a releasable chuck to engage the post on the trial prosthesis/rasp. Other instruments using handles with chucks to hold the trial prosthesis/rasp are shown on pages 19-23 of a brochure entitled "The Total System" from Zimmer U.S.A., Inc. of Warsaw, IN and in item 16 (Art. Nr. 5104) in a Brochure entitled "Trunnion-head total hip, operative technique" from ALLO PRO AG, Dorfstrasse 13, CH-6340 Baar/Zug. These chuck-type instruments are somewhat complicated to manufacture.

As part of "The PCA ™ Total Hip System", the Orthopaedics Division of Howmedica, Inc. of Rutherford, N.J. sells a Broach/Trial Stem Handle (Catalog No. 6079-0-000) for use with Broach/Trial Stems (Catalog Nos. 6079-0-001 to -007 and 6080-0-001 to -007) wherein the Handle receives the trunnion (post) on the Stem within a coupler which is closed by means of a moveable arm and held shut by moving the arm against the handle forming the main body. The coupler also has a pin extending from its end which appears to engage with the upper part of the Stem on which the part is located. Howmedica, Inc. also sells a Femoral Stem Extractor (Catalog No. 6079-6-400) which appears to be a locking set of pliers which is used to extract a femoral prosthesis stem from the femur, but does not appear to be useful for inserting a femoral trial prosthesis/rasp. These Howmedica devices are described on pages 8, 14-17, and 43 of their brochure number H4139 15M 1/84 B and on pages 42-49 of the surgical procedure (FIGS. 38a-44) found between pages 38 and 39 of that brochure.

Instruments employing screw-lock or push-pin mechanisms to affix the trial prosthesis-rasp to the handle are shown in brochure no. Y-BMT-010/090183 entitled "CFE TAPERLOC Hip System Surgical Technique" from Biomet, Inc. of Warsaw, IN (spring-loaded button), and in brochure no. 20M1183 0611-52 entitled "the AML ™ Total Hip System with Porocoat ®" as Broach Handle 2002-22 from DePuy, Inc. of Warsaw, IN (screw-lock). A femoral trial prosthesis and prosthesis Introducer/Extractor (Catalog No. JA 101) employing a locking pin which passes through the handle and the prosthesis is shown on page 90 (pages 43 and 44 show its use) of a brochure entitled "The Poro Metal cementless total hip prosthesis" distributed by Daumer International, P.O. Box 2229, 5632 Wermelskirchen, West Germany (page 91 shows a Catalog No. JA 601 reamer which is not detachable or useful as a trial prosthesis).

U.S. Pat. No. 3,818,514 to Clark (issued June 25, 1974) shows a protective sheath for a femoral prosthesis head which employs a sheath lined with a compressible material which fits about the prosthesis neck and possibly the head to securely engage the prosthesis and to aid in the insertion of the prosthesis into a prepared socket in the proximal femur. The compressible material prevents damage to the head when the prosthesis is pounded into the socket, but does allow the prosthesis to move relative to the sheath.

There is still a need for an instrument which will hold a femoral trial prosthesis/rasp rigidly in place during use, but which permits simple engagement and disengagement of the trial prosthesis/rasp.

SUMMARY OF THE INVENTION

It is one object of this invention to provide a proximal femoral trial prosthesis/rasp assembly for use in hip implant surgery. The novel handle assembly is easy to use, but is very effective in rigidly grasping the trial prosthesis/rasp while it is being used or removed from the prepared bone socket.

The novel handle assembly grips the trial prosthesis/rasp in a secure manner by clamping over and locking onto a post located on the upper end of the trial prosthesis/rasp. The handle assembly preferably comprises a straight member which has a recess on its lower end for reception of one half of the post in locking engagement and a pivotable lever attached to the straight member which contains an opposing recess which fits over the remainder of the post when a screw located in the upper end of the lever is tightened to bring the two lower ends of the handle together over the post. By turning the screw, the lower ends of the straight member and the lever are forced together and the trial prosthesis/rasp is rigidly affixed to the handle assembly in a rigid, but positive, manner. Preferably, the lower end of the handle assembly is designed to cooperatively engage the upper end of the trial prosthesis/rasp at a location separated from the post to further lend rigidity to the entire trial prosthesis/rasp assembly.

Upon completion of the preparation of the bone socket, the trial prosthesis/rasp is left in the femur and the handle is disengaged from the post simply by turning the screw. A trial reduction is then performed using the embedded trial prosthesis/rasp. Preferably, the post is adapted to receive a femoral prosthesis head for accomplishing the trial reduction. When the reduction is complete, the handle is reattached to the post and the femoral trial prosthesis/rasp is removed from the bone socket to permit fixation of a permanent proximal femoral prosthesis to the femur in the prepared bone socket.

BRIEF DESCRIPTION OF THE DRAWINGS

The above and other objects, features and advantages of the present invention will become apparent to those skilled in the art upon an examination of the following description and drawings.

In the Drawings:

FIG. 1 is an exploded view of the novel handle assembly of the present invention.

FIG. 2 is a side view of lever 302 taken along line 2—2.

FIG. 3 is a view of the lower end of lever 302 taken along line 3—3.

FIG. 4 is a side view of member 102 taken along line 4—4.

FIG. 5 is a view of the lower end of member 102 taken along line 5—5.

DETAILED DESCRIPTION OF THE INVENTION

Figures 6, 7:
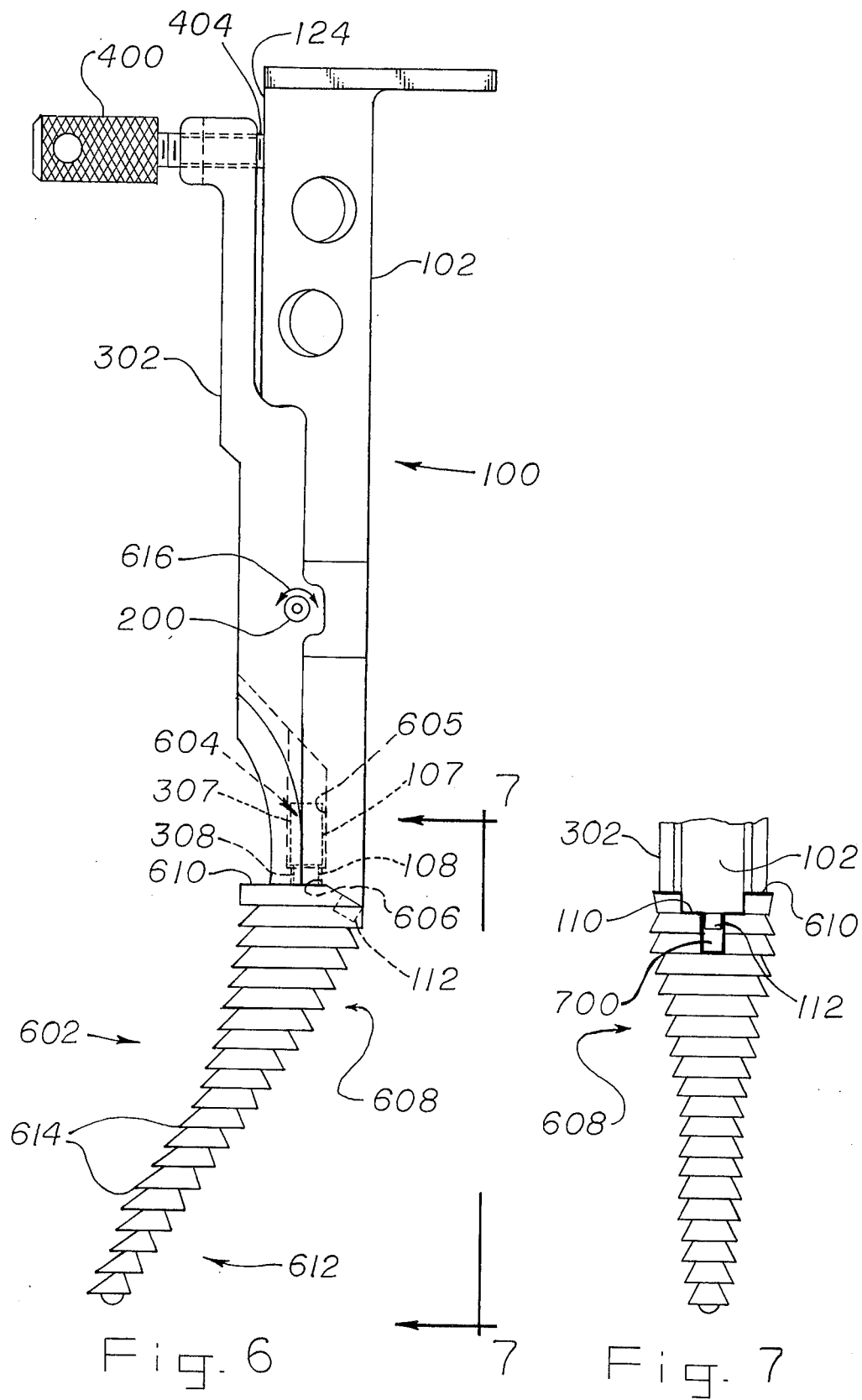
FIG. 6 is a plan view taken from the side of the trial prosthesis/rasp assembly of the present invention which comprises trial prosthesis/rasp 602 locked in handle assembly 100.
FIG. 7 is a partial side view of assembly of FIG. 6 taken along line 6—6.

Referring to the Drawings, FIG. 1 depicts a preferred form of the handle assembly 100 which is shown in exploded form and comprises an elongated member 102 having a lower end 104 containing a recess 106 wherein portion 107 of recess 106 is deeper than portion 108 to permit a close-fitting and locking engagement with one-half of post 604 as shown in FIG. 6. Surface 110 of end 104 is angled and thus "irregular" (i.e., not planar and perpendicular to the central long axis of member 102) to enable it to mate with surface 610 of trial prosthesis/rasp 602 and retain trial prosthesis/rasp 602 in a preselected orientation with respect to handle assembly 100. Projection 112 extends away from surface 110 and is adapted to closely fit within recess 700 in trial prosthesis/rasp 602 to further lend rigidity to the trial prosthesis/rasp 602 when it is engaged by handle assembly 100.

The upper end 114 of member 102 is of sufficient length to be manually engaged and can contain optional angled holes 116 and 118 to provide a means to extract the trial prosthesis/rasp assembly from the femur by placing a conventional "tommy bar" (not shown) through holes 116 or 118 and pulling on the bar as a handle. Holes 116 and 118 are placed at an angle (e.g., typically 15°) with respect to the prosthesis to be inserted so that the "tommy bar" can be used as an alignment guide to assist the surgeon in preparing the bone socket in accordance with well known surgical procedures for femoral rasps. One hole is angled for use on the left femur and the other is angled for use on the right femur.

The top of upper end 114 contains plate 120 which provides a surface on handle assembly 100 which can be struck by a hammer during surgery. Member 102 further contains a bore 122 located between ends 104 and 114. A small portion 121, 123 of member 102 in the vicinity of bore 122 is wider than the remainder of member 102 to facilitate pivoting of lever 302 relative to member 102.

Pin 200 is passed through bores 322, 122 and 323 to pivotally interconnect lever 302 with member 102. The diameter of pin 200 is slightly larger than the diameter of bores 322 and 323 and is slightly smaller than the diameter of bore 122 (or vice-versa) to permit pin 200 to be retained within the bores and to allow lever 302 to pivot relative to member 102. Pin 200 could also be a bolt or screw which is passed through bores 322, 122, and 323 and fixed within the bores by means of a locknut.

Lever 302 has a lower end 304 containing a recess 306 which is directly opposite to and corresponds with recess 106 when ends 304 and 104 are pivotally biased together. Recess 306 is composed of portion 307 which is deeper than portion 308 to permit a close-fitting and locking engagement with the other half of post 604. The recess need not engage the entire surface of the post as long as the post can be lockingly engaged within the recesses.

In FIG. 6, post 604 is shown in the preferred generally cylindrical configuration and, more preferably, portion 605 is adapted to receive a femoral prosthesis head for use in the aforementioned trial reduction procedure. Post 604 may be symmetrical from top to bottom (as shown) or can be tapered with a narrower top diameter which becomes wider as surface 610 is approached (e.g., a conventional "Morse" tapered post can be used). Post 604 need not be generally cylindrical, but can be square or diamond-shaped.

In the latter cases where a square or diamond-shaped post is used, surfaces 110 and 310 could be planar and perpendicular to the central long axis of member 102 rather than irregular and the trial prosthesis/rasp would be held in the desired preselected orientation with respect to the handle by means of the manner in which the recesses engage the post. In any case, the recesses must be designed to closely fit and lock the post to the lower ends of the lever and the elongated member forming the handle assembly.

Bores 322 and 323 are located between lower end 304 and upper end 314 of lever 302 in such a position and relative to bore 122 of member 102 such that end 304 is biased directly against end 104 when screw 400 which passes through threaded passage 326 in end 314 is turned to a sufficient extent that lower surface 404 contacts and presses against surface 124 of member 102 and pushes end 314 away from surface 124. Screw 400 can be hand tightened or a lever can be placed through bore 406 in knurled handle 408 to exert the desired degree of biasing force on lower ends 104 and 304. A hex head bolt or other screw or biasing means could also be used in place of screw 400 with equally effective results. As shown in FIG. 6, recesses 106 and 306 are situated directly opposite each other when ends 104 and 304 are biased together to firmly engage post 604. Screw 400 is simply turned in the opposite direction when the surgeon desires to release post 604, and thus the trial prosthesis/rasp 602, from the handle assembly 100.

Member 102, pin 200, lever 302, and screw 400 are preferably made of noncorrosive, surgical grade of metal such as surgical stainless steel or some other metal commonly used for the construction of surgical instruments. Trial prosthesis/rasp 602 can also be made of such a metal. As long as the material is medically acceptable and of sufficient strength to be useful, the actual nature of the material used forms no part of the present invention.

FIG. 2 depicts a side view of the outer surface of lever 302 and FIG. 3 shows an end view of lever 302 with interior structures shown as dotted lines so that the positioning of the various bores and recess 306 can more readily be understood. Similarly, FIG. 4 depicts a view of the side of member 102 showing surface 124. FIG. 5 shows an end view of member 102 viewed from end 104.

FIG. 6 depicts handle assembly 100 in locking engagement with trial prosthesis/rasp 602 to form the trial prosthesis/rasp assembly of the present invention. Trial prosthesis/rasp 602 is an elongated member having a tapered and slightly curved configuration extending from a relatively wide upper end 608 towards a narrower lower end 612. Its configuration is generally similar to the configuration of the proximal femoral prosthesis which is ultimately to be implanted in the femoral bone socket. Trial prosthesis/rasp 602 has a cutting portion extending substantially over its entire surface although in some cases it may be desirable to only have the cutting portion extend from upper end 608 downward for one half to two-thirds of its length. Trial prosthesis/rasp 602 contains a plurality of cutting teeth 614 forming the cutting portion of the trial prosthesis/rasp 602. The cutting teeth may be coarse, fine or a combination of different types. Coarse cutting teeth are shown to simplify the drawing.

In the preferred embodiment shown, generally cylindrical post 604 has a wider portion 605 and a narrower portion 606 which is engaged by recesses 106 and 306 in a close-fitting and locking manner. Surface 610 of trial prosthesis/rasp 602 mates with surfaces 110 and 310 to hold the trial prosthesis/rasp 602 in a preselected orientation with respect to the handle assembly 100. The direction in which lever 302 pivots about pin 200 is shown by reference arrows 616.

FIG. 7 more clearly shows the optional, but preferred, manner in which projection 112 is closely engaged within recess 700 to further rigidly engage trial prosthesis/rasp 602 and align it with handle assembly 100.

The manner in which the femoral trial prosthesis/rasp assembly of the present invention is used has been briefly described above in the Summary and further details on the use of a trial prosthesis/rasp instrument will be readily apparent to those skilled in the art as evidenced by some of the surgical procedure brochures noted in the Background of the Invention, supra.

Other modifications and variations in the trial prosthesis/rasp assembly of the present invention will become apparent to those skilled in the art from an examination of the above specification and accompanying drawings. Therefore, other variations of the present invention may be made which fall within the scope of the appended claims even though such variations were not specifically discussed above.

That which is claimed is:

1. In combination, a femoral trial prosthesis/rasp assembly for use in the implantation of a proximal femoral prosthesis, said assembly comprising:

a trial prosthesis/rasp comprising a first elongated member having a tapered and slightly curved configuration extending from a relatively wide upper end towards a narrower lower end, said member having a cutting portion extending from said upper end downward over at least a portion of its surface and having cutting teeth projecting from the surface of said cutting portion, said first member further having a post affixed to said upper end, and a handle assembly adapted to releasably engage said post and said upper end of the first member in a predetermined orientation with respect to said handle assembly, said handle assembly comprising:

a second elongated member having a lower end which contains a recess adapted to receive a portion of said post in close-fitting and locking engagement, said post having a configuration which permits said locking engagement, said second member having an upper end which is adapted to be manually engaged and to be struck by a hammer to facilitate use of the trial prosthesis/rasp to form a prosthesis socket in the femur, a lever having a lower end which contains a recess adapted to receive a portion of the post which is opposite that which is engaged by the recess in the second elongated member, a second opposing end, and a pivot pin means interconnecting said lever and said second member at a point between the ends thereof whereby the post is received and rigidly engaged within said recesses when the lower end of said lever is biased in the direction of the lower end of the second member by a screw means which cooperatively engages and passes through the upper end of said lever and is adapted to bias said upper end of the lever away from the upper end of the second member and cause the opposing lower ends of the lever and second member to close and engage said post when the screw means is turned in one direction and to permit said lower ends to open and release said post when the screw means is turned in the opposite direction.

2. The femoral trial prosthesis/rasp assembly as claimed in claim 1 wherein the upper end of said prosthesis is irregular and adapted to mate with an opposing irregular surface located on said lower ends of said handle and lever to establish said preselected orientation of the femoral trial prosthesis/rasp.

3. The femoral trial prosthesis/rasp assembly as claimed in claim 2 wherein said post has a generally cylindrical shape and a portion of the post closest to said upper end of the trial prosthesis/rasp is smaller in diameter than the remainder of the post.

4. The femoral trial prosthesis/rasp assembly as claimed in claim 3 wherein the lower end of said second elongated member includes a projection extending away from said lower end which is adapted to be received by and closely fit within a third recess located in said upper end of said first elongated member to establish said preselected orientation of the femoral trial prosthesis/rasp.

5. The femoral trial prosthesis/rasp assembly as claimed in claim 1 wherein said post is adapted to receive a femoral prosthesis head.

6. The femoral trial prosthesis/rasp assembly as claimed in claim 3 wherein said post is adapted to receive a femoral prosthesis head.

* * * * *